(12) United States Patent
Stefanov (10) Patent No.: US 11,116,912 B2
(45) Date of Patent: Sep. 14, 2021

(54) NEEDLE SHIELD MECHANISM AND A MEDICAMENT DELIVERY DEVICE COMPRISING THE NEEDLE SHIELD MECHANISM

(71) Applicant: Carebay Europe Ltd, Sliema (MT)

(72) Inventor: Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 146 days.

(21) Appl. No.: 15/777,573

(22) PCT Filed: Nov. 3, 2016

(86) PCT No.: PCT/EP2016/076560
§ 371 (c)(1),
(2) Date: May 18, 2018

(87) PCT Pub. No.: WO2017/084883
PCT Pub. Date: May 26, 2017

(65) Prior Publication Data
US 2021/0196902 A1    Jul. 1, 2021

(30) Foreign Application Priority Data
Nov. 20, 2015 (SE) .................................. 1551512-5

(51) Int. Cl.
*A61M 5/32* (2006.01)
*A61M 5/20* (2006.01)

(52) U.S. Cl.
CPC ........ *A61M 5/3234* (2013.01); *A61M 5/2033* (2013.01); *A61M 5/3202* (2013.01)

(58) Field of Classification Search
CPC .............. A61M 5/3234; A61M 5/2033; A61M 5/3202; A61M 5/3243; A61M 5/3245; A61M 2005/2073; A61M 2005/208
See application file for complete search history.

(56) References Cited

U.S. PATENT DOCUMENTS 8,551,054 B2    10/2013    Guillermo
9,605,410 B2    3/2017    Kitamura
(Continued)

FOREIGN PATENT DOCUMENTS

CN    103099069 A    6/2011
EP    2823839 A1    1/2015
(Continued)

OTHER PUBLICATIONS

Search Report issued in Swedish Patent Application No. 1551512-5 dated May 6, 2016.
(Continued)

*Primary Examiner* — Bhisma Mehta
*Assistant Examiner* — Neeraja Gollamudi
(74) *Attorney, Agent, or Firm* — McDonnell Boehnen Hulbert & Berghoff LLP (57) ABSTRACT

Needle shield mechanism for an auto-injector comprising, a tubular housing (10), a needle shield (12) movably arranged in the housing (10), between a retracted state and an extended position, a releasable spring-biased container carrier assembly movably arranged relative to the housing (10) from an initial position to a penetrating position, wherein the container carrier assembly prevents the needle shield (12) from moving to the extended position when the container carrier assembly is in the initial position, and wherein the container carrier assembly allows the needle shield (12) to move to the extended position when the container carrier assembly is in the penetrating position.

17 Claims, 10 Drawing Sheets

(56) References Cited

U.S. PATENT DOCUMENTS

| | | |
|---|---|---|
| 9,861,754 B2 | 6/2018 | Holmqvist |
| 2005/0101919 A1 | 9/2005 | Brunnberg |
| 2005/0203466 A1 | 9/2005 | Hommann et al. |
| 2009/0240804 A1 | 9/2009 | Zhao et al. |
| 2010/0191217 A1 | 7/2010 | Hommann et al. |
| 2014/0257193 A1* | 9/2014 | Bostrom ............. A61M 5/3204 604/197 |
| 2015/0273162 A1 | 10/2015 | Holmqvist |
| 2016/0015901 A1 | 1/2016 | Plumptre |
| 2016/0051765 A1 | 2/2016 | Morris et al. |
| 2016/0067411 A1 | 3/2016 | Morris |
| 2017/0136192 A1* | 5/2017 | Stefansen ........... A61M 5/2033 |
| 2018/0344937 A1 | 12/2018 | Loof et al. |

FOREIGN PATENT DOCUMENTS

| | | |
|---|---|---|
| TW | 201417853 A | 5/2014 |
| TW | 201431577 A | 8/2014 |
| TW | 201509458 A | 3/2015 |
| TW | 201509467 A | 3/2015 |
| TW | 201521808 A | 6/2015 |
| WO | 2006021932 A1 | 3/2006 |
| WO | 2009063030 A1 | 5/2009 |
| WO | 2015011787 A1 | 1/2015 |

OTHER PUBLICATIONS

Search Report issued in Taiwanese Patent Application No. 105136711 dated Aug. 4, 2017.

* cited by examiner

NEEDLE SHIELD MECHANISM AND A MEDICAMENT DELIVERY DEVICE COMPRISING THE NEEDLE SHIELD MECHANISM

CROSS REFERENCE TO RELATED APPLICATIONS

The present application is a U.S. National Phase Application pursuant to 35 U.S.C. § 371 of International Application No. PCT/EP2016/076560 filed Nov. 3, 2016, which claims priority to Swedish Patent Application No. 1551512-5 filed Nov. 20, 2015. The entire disclosure contents of these applications are hereby incorporated by reference into the present application.

TECHNICAL FIELD

The present invention relates to a needle shield mechanism for an auto-injector and in particular to a needle shield mechanism providing a safer needle covering feature.

BACKGROUND OF THE INVENTION

There are many injectors on the market where the aim is to have a high degree of functionality and automatic features, often relating to penetration, injection, setting of dose, priming and covering of the needle after use. At the same time there is a demand on robustness, repeatability and reliability regarding the function, which sometimes may be difficult to meet when dealing with complex multi-function devices involving many interacting components. Further, when there are demands on low production costs, especially for devices that are to be used only once, the picture becomes even more complex.

In patent literature there are numerous solutions to injection devices, the bulk of which never enter the market due to that they do not meet the demands in one way or the other. There is therefore a continuous search for solutions that provide the desired functions and at the same time fulfil the functional and/or economical demands.

Many devices having multi-functions that work in sequence, such as for example penetration, followed by injection, followed by needle protection, have a subsequent sequence triggered at the end of a previous sequence, for example when the needle has reached full penetration depth, the injection sequence is triggered.

In WO-A1-2009063030, an active triggering withdrawal mechanism is capable of allowing the means for automatically withdrawing the needle to be triggered when the injection device starts to be removed from an injection site. However, if the user unintentionally removes the injection device before injection has been completed, the needle retraction will not be allowed until the upper edge of the plunger rod passes the outwardly directed protrusions of the flexible arms holding the retraction release ring. Then there is a problem of having to handle an exposed and possibly contaminated needle until the retraction is triggered.

Although this problem has been recognized in US20100191217, a spring-biased needle-protecting sleeve has been proposed rather than an automatic withdrawal of the needle. However, the spring force for shifting the needle protecting sleeve in the distal direction from the proximal position increases during movement of an advancing drive element. Thus, the user has to hold the injection device with a large force which would be difficult for some users handling the device, especially for children or elder people.

It is an object of the present invention to provide an injection device having a needle shield mechanism, which is user friendly and safe and which overcomes or at least reduces the problems identified above.

BRIEF DESCRIPTION OF THE INVENTION

In the present application, when the term "rearward" is used, this refers to the direction pointing away from the dose delivery site. When the term "rear part/end" is used, this refers to the part/end of the delivery device, or the parts/ends of the members thereof, which under use of the medicament delivery device is/are located furthest away from the dose delivery site. Correspondingly, when the term "forward" is used, this refers to the direction pointing to the dose delivery site. When the term "front part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

The aim of the present invention is to provide an injector that fulfils the safety demands that are put on such devices and which ensure that the needle and the user are fully protected to prevent accidental needle sticks.

According to a main aspect of the invention it is characterized by the features of the independent patent claim. Further advantageous features are subjects of the dependent claims.

According to a main aspect of the invention it is characterised by a needle shield mechanism for an auto-injector, which needle shield mechanism comprises, a longitudinally elongated, generally tubular housing having a forward end and a rear end, a generally tubular needle shield movably arranged in the housing between a retracted state and an extended position, a releasable spring-biased container carrier assembly for accommodating a medicament container, wherein the container carrier assembly is movably arranged in the housing and is movable relative to the housing from an initial position to a penetrating position, and is also movable relative to the needle shield, wherein the container carrier assembly prevents the needle shield from moving to the extended position when the container carrier assembly is in the initial position, and wherein the container carrier assembly allows the needle shield to move to the extended position when the container carrier assembly is in the penetrating position.

In a further aspect of the invention the needle shield is spring-biased and comprises a deflectable locking element, which deflectable locking element is radially deflectable and comprises an outwardly directed protrusion.

In a further aspect of the invention the container carrier assembly prevents the deflectable locking element from deflecting radially when the container carrier assembly is in the initial position and the needle shield is in the retracted state.

In a further aspect of the invention the container carrier assembly comprises a container carrier, configured to accommodate a medicament container, the container carrier assembly further comprises an intermediate drive member fixedly connected to the container carrier.

In a further aspect of the invention a component of the container carrier assembly, such as the container carrier or the intermediate drive member is adjacent and radially inside the deflectable locking element of the needle shield when the container carrier assembly is in the initial position and the needle shield is in the retracted state, thereby preventing the deflectable locking element from deflecting radially inwards.

In a further aspect of the invention the outwardly directed protrusion of the deflectable locking element interacts with a ledge of an inner surface of the housing when the needle shield is in the retracted state.

In a further aspect of the invention the outwardly directed protrusion has a chamfered surface which interacts with the ledge.

In a further aspect of the invention a component of the container carrier assembly, such as the container carrier or the intermediate drive member is in front of, and radially inside, the deflectable locking element of the needle shield when the container carrier assembly is in the penetrating position and the needle shield is in the retracted state, thereby allowing the deflectable locking element to deflect radially inwards, and allowing the needle shield to move to the extended position.

In a further aspect of the invention the needle shield comprises a locking member and the housing comprises a corresponding locking member, and wherein the locking member and the corresponding locking element engage each other when the needle shield is in the extended position to lock the needle shield in the extended position.

In a further aspect of the invention the outwardly directed protrusion of the deflectable locking element interacts with a forward ledge of an inner surface of the housing when the needle shield is in the extended position.

In a further aspect of the invention a component of the container carrier assembly, such as the container carrier or the intermediate drive member is adjacent and radially inside the deflectable locking element of the needle shield when the container carrier assembly is in the penetrating position and the needle shield is in the extended position, thereby preventing the deflectable locking element from deflecting radially inwards.

In a further aspect of the invention the needle shield in the retracted state is movable between a partially extended position and a triggering position.

In a further aspect of the invention the container carrier assembly may be released to move to the penetrating position when the needle shield is in the triggering position.

The needle shield mechanism provides a safety feature in that it allows the needle to be covered and protected, thereby maintaining safety even if the injection device is accidentally lifted during dose administration.

Furthermore, the spring-bias on the needle shield does not increase as the injection progresses since the needle shield uses its own drive force member.

The needle shield mechanism is a cost-effective assembly of components that operates in a safe and reliable sequence of steps, thus ensuring that the user is safe and protected at all times.

These and other features and advantages of the present invention will become apparent from the following detailed description and the drawings.

BRIEF DESCRIPTION OF THE DRAWINGS

In the following detailed description, reference will be made to the drawings, of which

DETAILED DESCRIPTION OF THE INVENTION

Figures 1A, 1B:
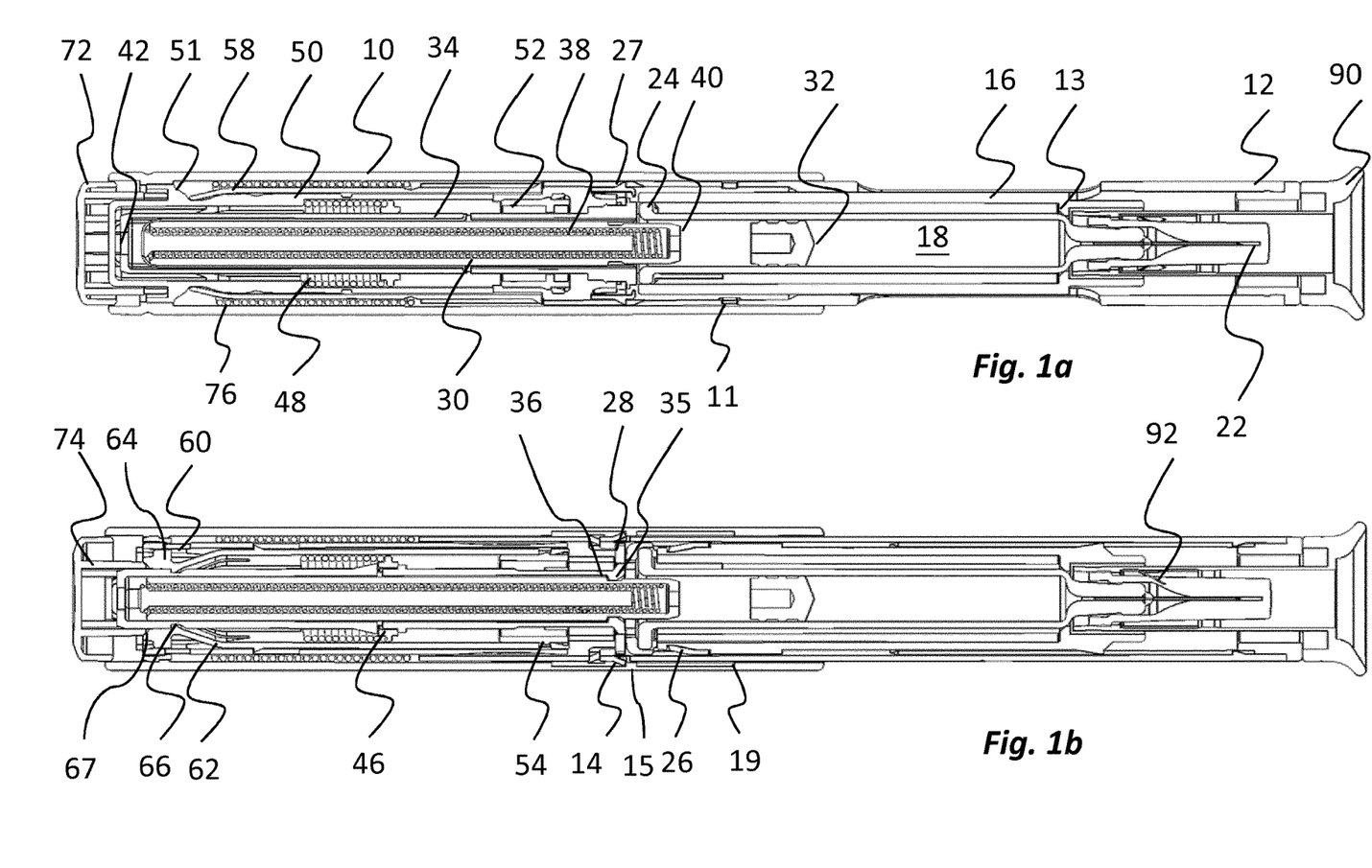
FIG. 1 is a longitudinal cross-section of an auto-injector comprising the invention.

Referring to FIG. 1, the invention may generally be embodied by a needle shield mechanism for an auto-injector, having a generally tubular housing 10. In a front end of the housing 10, to the right in FIG. 1, a generally tubular needle shield 12 with a forwardly directed contact part is movably arranged in the housing 10 between a retracted state and a forward extended position. A first drive element 76, such as a spring, biases the needle shield 12 forward towards the extended position. A container carrier assembly is coaxially arranged in the housing 10 and is movable relative to the housing 10 between an initial position, and a forward, penetrating position. The initial position is the most rearward position of the container carrier assembly relative to the housing, and the penetrating position is the most forward position of the container carrier assembly relative to the housing.

The positions of the needle shield 12 and of the container carrier assembly may be defined according to the following:

In the retracted state, the needle shield 12 is movable between a partially extended position and a triggering position. In the partially extended position, an auto-injector in which the needle shield is comprised, is typically locked, or inactive, and a contact part of the needle shield protrudes slightly in front of the auto-injector. In the triggering position, the needle the contact part of the needle shield is flush with the front of the auto-injector, and the auto-injector is unlocked and may be activated to perform a penetration and injection sequence. A needle 22 attached to the container carrier assembly is completely shielded when the container carrier assembly is in the initial state. The needle protrudes from the front of the auto-injector/needle shield when the container carrier assembly is in the penetrating position.

In the extended position, the needle shield is at its most forward position relative to the housing 10. The needle shield 12 may only attain this position if the container carrier assembly is in the penetrating position. When the needle shield 12 is in the extended position, the needle 22 is completely shielded by the needle shield 12, i.e. it does not protrude in front of the needle shield 12. The needle shield 12 locks in the extended position and is prevented from return movement towards the retracted state.

Figure 3A:
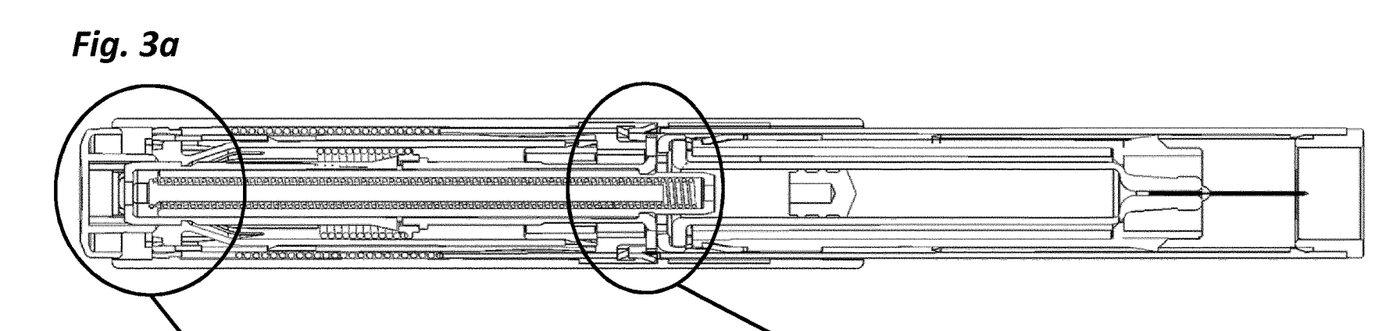
FIG. 3 shows a detailed cross-sectional view of an embodiment of the invention.
Figure 3B:
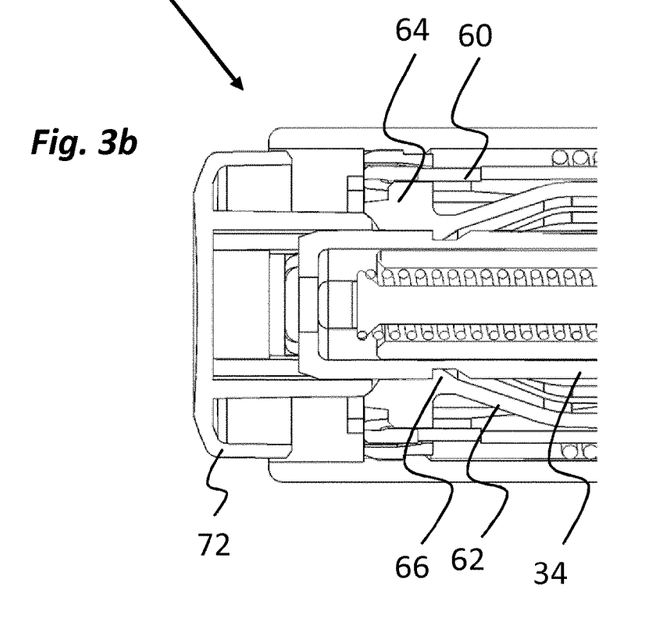
Figure 3C:
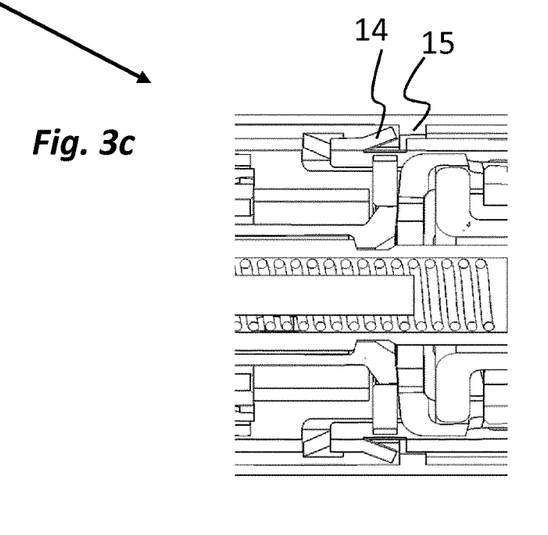

When in the retracted state, the needle shield 12 is prevented from moving to the extended position by an outwardly directed protrusion 14 on an outer surface of a deflectable locking member 17 of the needle shield 12, co-operating with a ledge 15 on an inner surface of the housing 10, FIG. 3c. A protective cap 90 is releasably attached and inserted into the front end of the needle shield 12.

The container carrier assembly is located coaxial with, and radially inside, the needle shield 12. The container carrier assembly may comprise a container carrier 16, an intermediate locking member 34, a hold-and-release member 28, a spring holder ring 46, and a second drive member 48, such as a spring. The container carrier assembly is forwardly spring-biased by, the second drive member 48, towards the penetrating position.

Inside the container carrier 16 a container 18, containing medicament, may be arranged. The container 18 is prevented from moving forward relative to the container carrier 16 by a circumferential ledge 13, acting against a shoulder of the container 18. The container 18 may be a syringe, a cartridge, an ampoule, or the like. The front end of the container 18 can be arranged with attachment means for attaching a needle 22 to the container 18. A rear end of the container 18 is arranged with a flange 24 seated adjacent a rear end of the container carrier 16.

The device comprises activation means arranged to be interactively connected to the needle shield 12 and capable of, upon manual activation, initiating a penetration sequence, i.e. a forward movement of the container carrier assembly towards the penetrating position, as will be explained in detail below. The activation means comprises at least one rearwardly directed deflectable element 62 of a penetration sleeve 50 fixedly associated with the housing 10, which release element 62 has an inwardly extending ledge 66. The activation means further comprises at least one recess 60 of a generally tubular lockout member 58, a circumferential groove 68 of an intermediate drive member 34, and a trigger button 72 having at least one longitudinal, forwardly extending element 74 facing the release element 62.

Further, the device comprises penetration means interactively connected to the activation means and capable of performing an automatic penetration of the needle 22 as will be explained in detail below. The penetration means comprises tongues 26 arranged on the intermediate drive member 34, in snap-fit engagement with the container carrier 16 and the second drive element 48, arranged between the intermediate drive member 34, or a spring holder ring 46 fixedly associated with the intermediate drive member 34, and an inner rear wall of the penetration sleeve 50. The spring holder ring may also be an integrated structural protrusion of the intermediate drive member 34.

The device also comprises injection means interactively connected to the penetration means and capable of triggering and performing an automatic injection of the medicament as will be explained in detail below. The injection means comprises at least one flexible element 36 arranged on the intermediate drive member 34 and where flexible element 36 is arranged with an inwardly directed ledge 35. The injection means further comprises a plunger 30 having a receiving element 37, e.g. a circumferential groove, in which the inwardly directed ledge 35 of the intermediate drive member 34 is positioned when the device is unarmed; and a third drive element 38, such as a spring, and a guide rod 33, arranged compressed inside the plunger 30 between a front wall 40 of the plunger 30 and a rear wall 42 of the intermediate drive member 34.

Further, as stated above, the device comprises a needle shield mechanism interactively connected to the penetration means and capable of triggering and performing an automatic needle shielding action upon movement of the container carrier assembly, as will be explained in detail below. The needle shield 12 is spring-biased by the first drive element 76, which is arranged between a rear end of the needle shield 12 and protrusions 78 arranged on the housing 10 or on the penetration sleeve 50 associated therewith.

The plunger 30 extends into the container 18 with a forward end abutting a piston 32. The rear end of the plunger 30 is surrounded by the intermediate drive member 34 which is fixedly connected to the container carrier by a snap-fit engagement via the tongues 26 of the intermediate drive member 34. Before an injection is triggered, the inwardly directed ledge 35 of the flexible element 36 of the intermediate drive member 34 is positioned in a receiving element 37, such as a circumferential groove, of the plunger 30, FIG. 2. The flexible element 36 and the inwardly directed ledge 35 are held in this position by a hold-and-release element 28 which is releasably attached to the intermediate drive member 34. When the plunger 30 is released by the hold-and-release element 28 the flexible element 36 and the inwardly directed ledge 35 disengage from the receiving element 37, allowing the plunger 30 to move forward relative to the intermediate drive member 34, under the bias of the third drive element 38, to expel medicament from the container 18.

As previously mentioned, the second drive element 48 is arranged between the intermediate drive member 34, or a spring holder ring 46 fixedly associated therewith, and the inner rear wall of the penetration sleeve 50. A spring retainer 52 is in snap-fit engagement with the penetration sleeve 50, by outwardly directed protrusions 54, extending into recesses 56 of the penetration sleeve 50. Radially outside the penetration sleeve 50 the lockout member 58 is arranged. At a rear part of the lockout member 58, the recess 60 is arranged adjacent the release element 62 of the penetration sleeve 50, which release element 62 is arranged with an outwardly extending protrusion 64 as well as an inwardly extending ledge 66. In the initial position these inwardly extending ledge 66 is in contact with the circumferential groove 68 of the intermediate drive member 34. The rear part of the release element 62 is further arranged with a rearwardly inclined surface 67.

At a rear end of the housing 10 the trigger button 72 is slidably arranged, having the longitudinal, forwardly extending element 74, which is arranged with an inclined surface facing the rearwardly inclined surface 67 of the release element 62. Since an inner wall of the lockout member 58 is arranged adjacent the release element 62, the release element 62 cannot be moved radially outwards. The release element 62 consequently prevents the trigger button 72 from being moved forward, FIG. 3b.

The device is intended to function as follows. When in the retracted state, the needle shield 12 is positioned inside the housing 10 and held in place by the protrusion 14 of the needle shield 12 acting against the ledge 15 of the housing 10, FIG. 1, 3c. The protective cap 90 is attached to the front end of the medicament delivery device, in contact with the needle shield 12 and surrounding the needle 22 with its needle sheath. When the protective cap 90 is removed, the needle sheath is also removed by a needle sheath grabber 92.

In order to initiate a penetration sequence, the user presses the front end of the needle shield 12 against the injection site, causing a movement of the needle shield 12 from the partially extended position to the triggering position, and pushes the trigger button 72. The pressing of the needle shield 12 to the triggering position causes the lockout member 58 to be moved the same distance as the needle shield 12, since the upper end of the needle shield 12 is in contact with the lower end of the lockout member 58.

Figure 2:
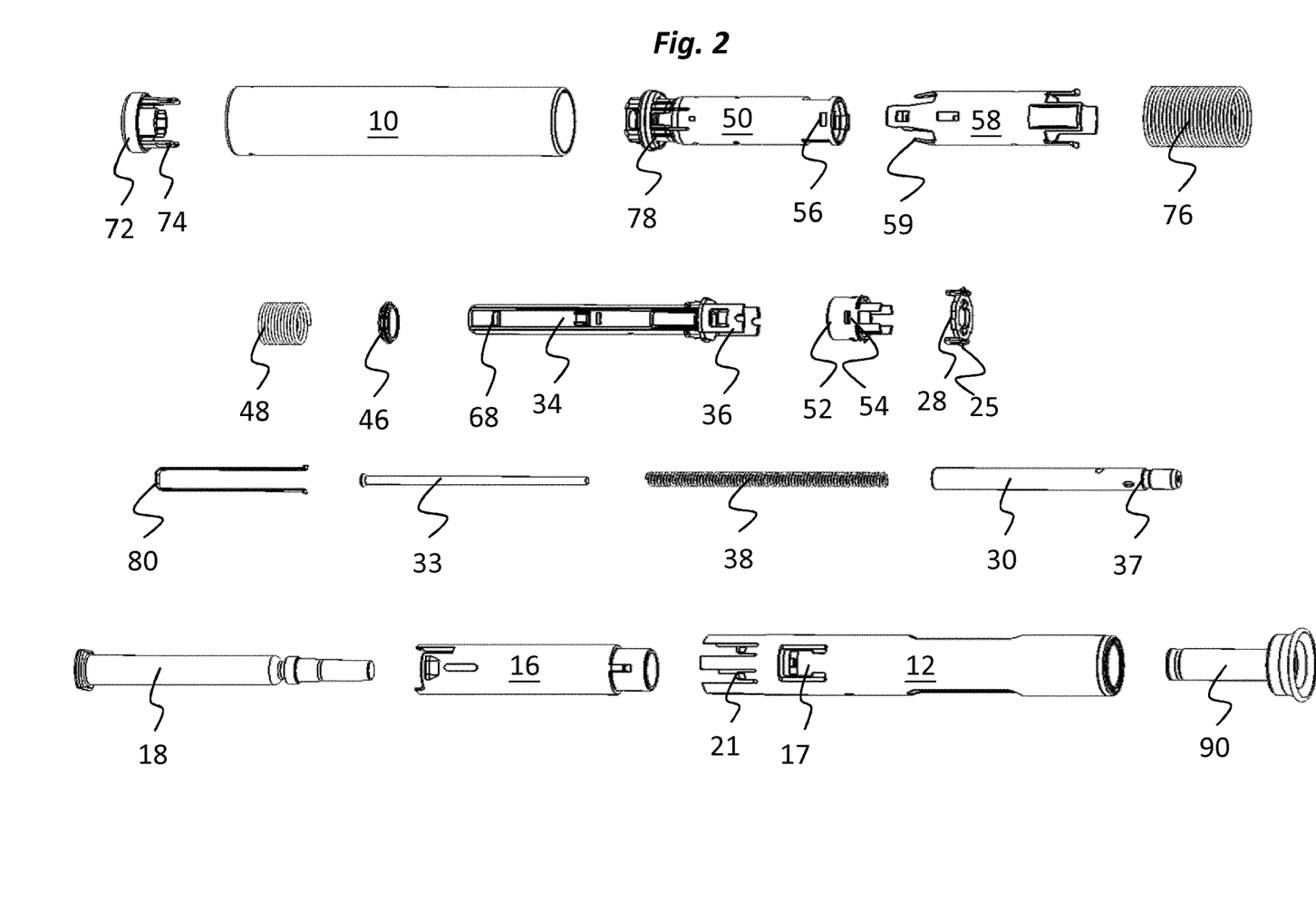
FIG. 2 is an exploded view of the auto-injector of FIG. 1.

If the device is lifted or removed from the injection site without pushing the trigger button 72, the lockout member 58 and the needle shield 12 are resiliently moved back to the partially extended position due to the interaction between tongues 59 of the lockout member 58 and forwardly inclined surfaces 51 of the penetration sleeve, FIGS. 1, 2.

Figure 4A:
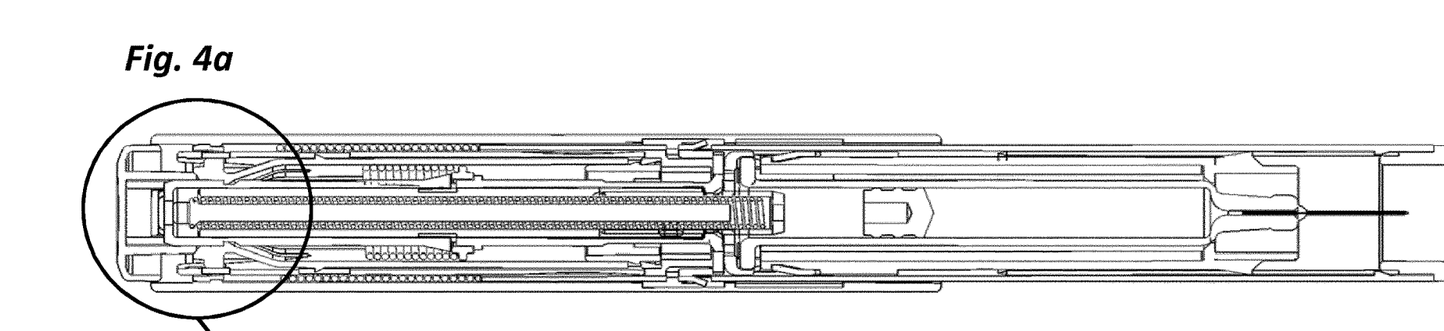
FIGS. 4-8 show cross-sectional views of different functional steps of the device of FIG. 1.
Figure 4B:
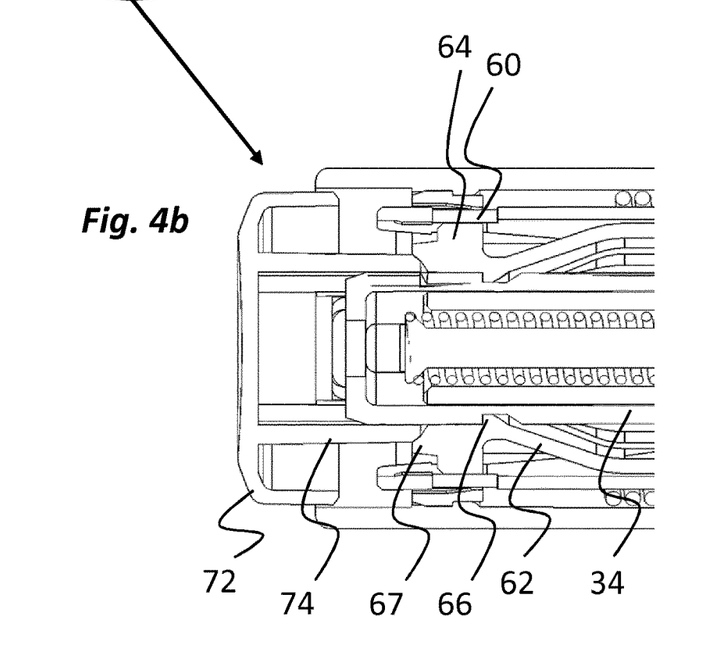
Figure 5A:
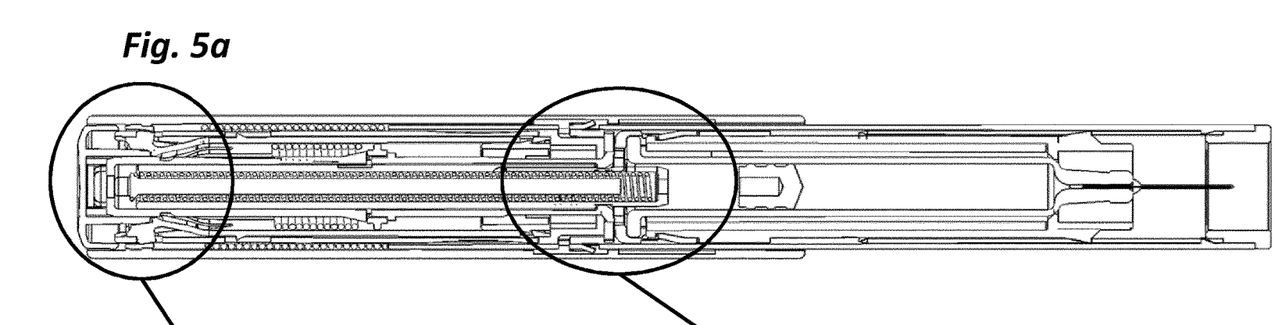
Figure 5B:
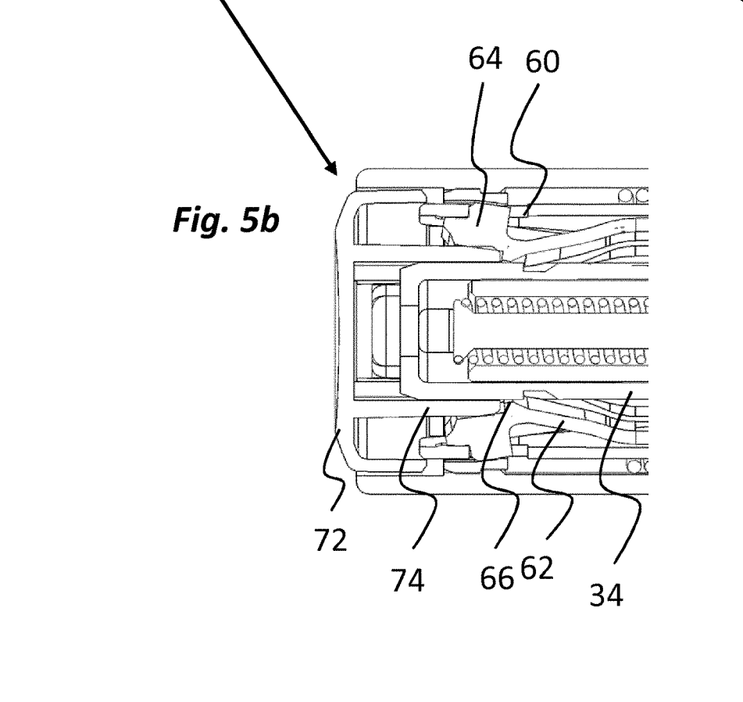

Referring to FIG. 4, when moved rearwardly by the needle shield 12, the movement of the lockout member 58 causes its recess 60 to align with the outwardly extending protrusion 64 of the release element 62 of the penetration sleeve 50, which enables the trigger button 72 to be depressed by the user whereby the inclined surfaces of the longitudinally extending elements 74 act on the rearwardly inclined surfaces 67 of the release element 62, causing them to move radially outwards, FIG. 5. The outward movement is impossible when the lockout member 58 has not been moved since the outwardly extending protrusions 64 of the release element 62 would then be blocked by the inner surface of the lockout member 58.

When the release element 62 moves radially outwards the inwardly directed ledge 66 of the release element 62 is moved out of contact with the circumferential groove 68 of the intermediate drive member 34 which is then moved forward by the second drive element 48 acting on the intermediate drive member 34 or on the spring holder ring 46. Thus the intermediate drive member 34, the spring holder ring 46, the plunger 30 arranged inside the intermediate drive member 34, the container carrier 16 connected to the intermediate drive member 34, the hold-and-release element 28 and the container 18 are moved forward causing a penetration of the needle 22 into the injection site, FIG. 6.

Figure 7A:
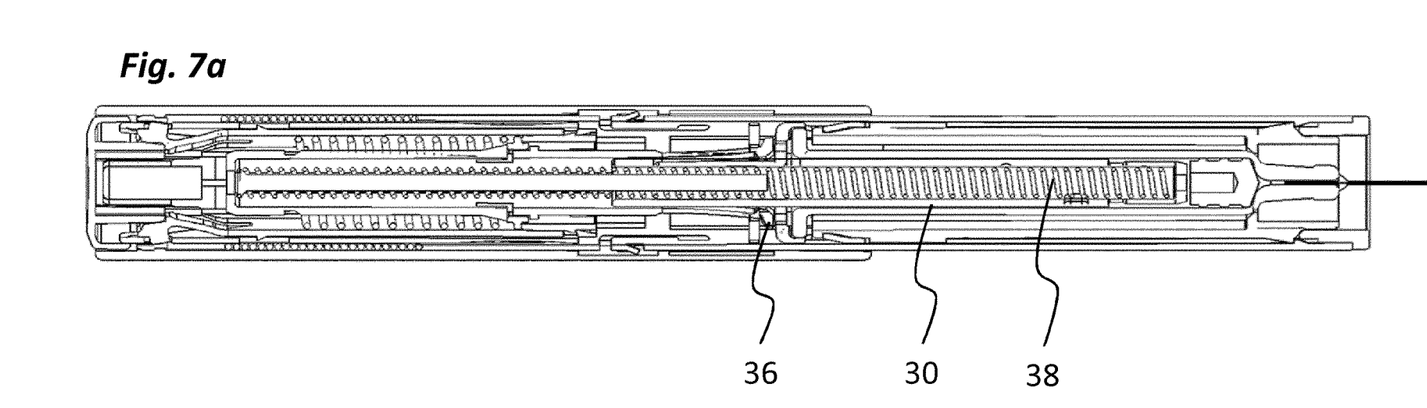
Figure 7B:
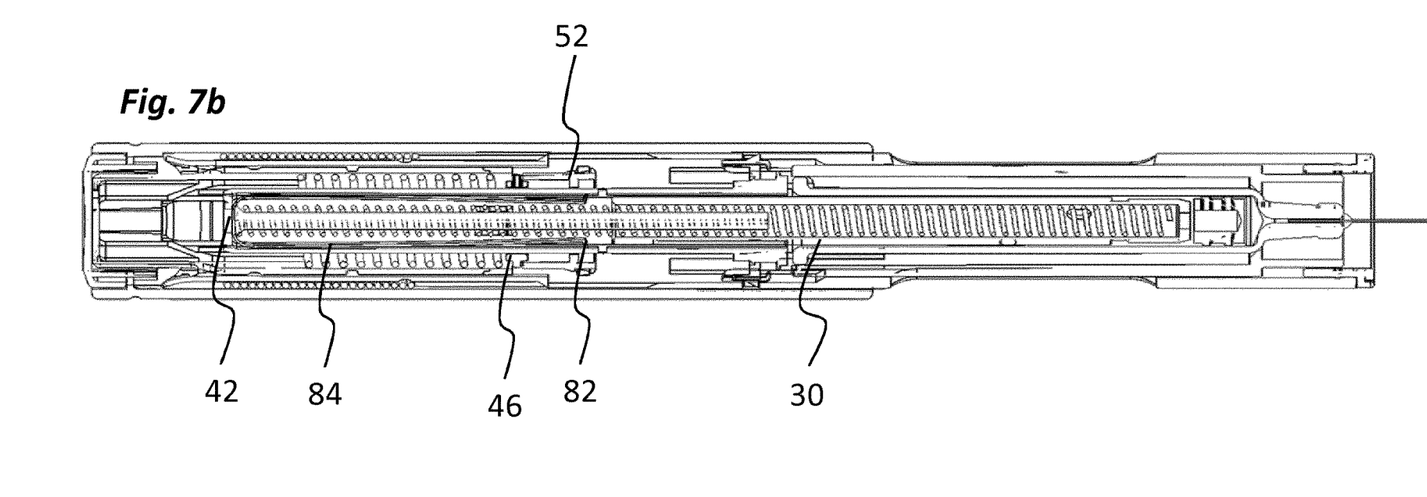

At a certain depth the hold-and-release element 28 is stopped by the engagement of protrusions 27 of its flexible arms 25 into a recess 11 on the inner surface of the needle shield 12, FIG. 1, which frees the flexible element 36 because the intermediate drive member 34 continues to move a short distance relative to the hold-and-release element 28. In other words, the flexible element 36 passes the hold-and-release element 28 due to the continued movement of the intermediate drive member 34. The freeing of the flexible element 36 causes it to flex outwards radially, whereby the inwardly directed ledge 35 is moved out of contact with the receiving element 37 on the plunger 30. The movement of the intermediate drive member 34, and thus the penetration, is stopped when the intermediate drive member 34 or a spring holder ring 46 associated therewith contacts the spring retainer 52, FIG. 7, which is snap-fit to the penetration sleeve 50. Alternatively, a protrusion at a front end of the needle carrier 16 may stop against a recess at a front part of the inner surface of the needle shield 12.

The release, or disengagement, of the inwardly directed ledge 35 of the intermediate drive member 34 from the receiving element 37 of the plunger 30 triggers an injection by releasing the plunger 30. Due to the force of the third drive element 38, the plunger 30 pushes the piston 32 forward, causing an injection, FIG. 7. When the injection has been completed an indication may be given to the user such as an audible indication, that the injection has been completed.

Figure 5C:
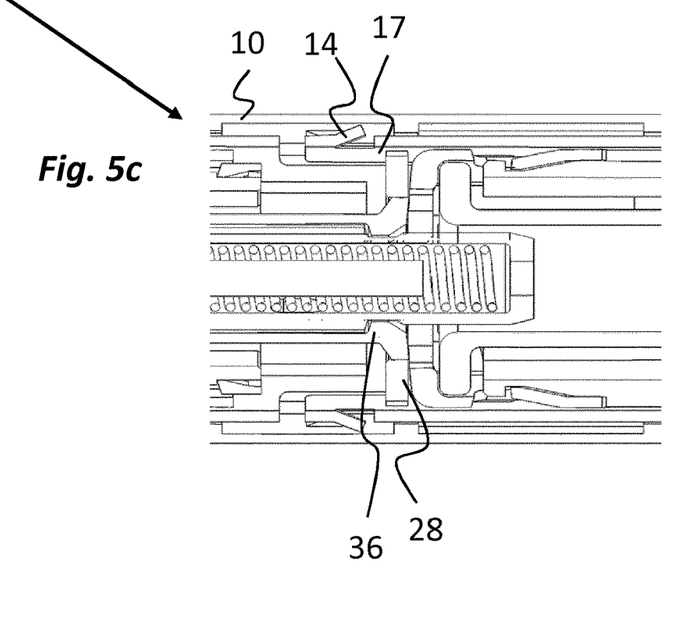
Figure 9:
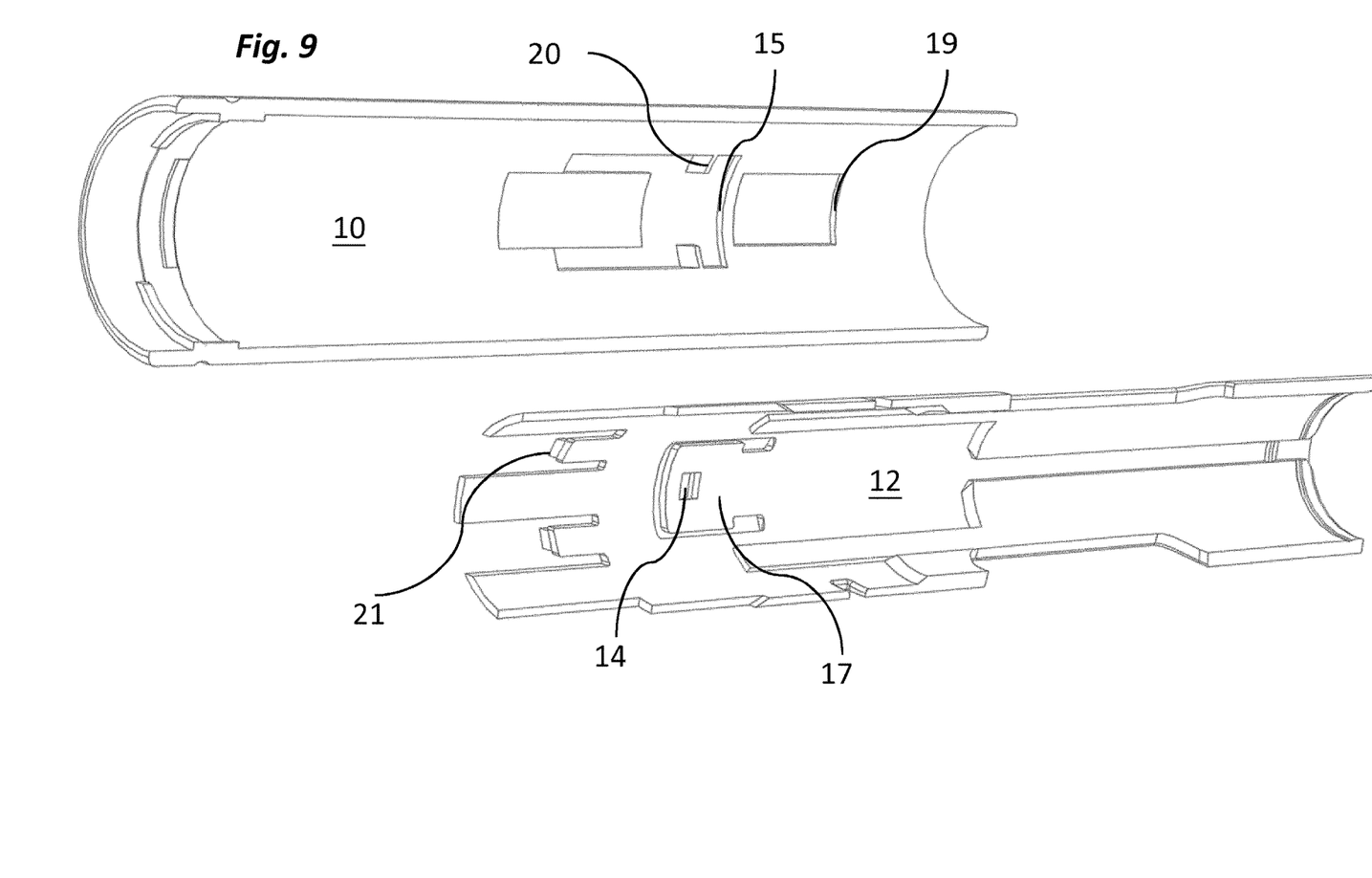
FIG. 9 shows a cross-sectional perspective view of the needle shield and the housing.
Figure 10:
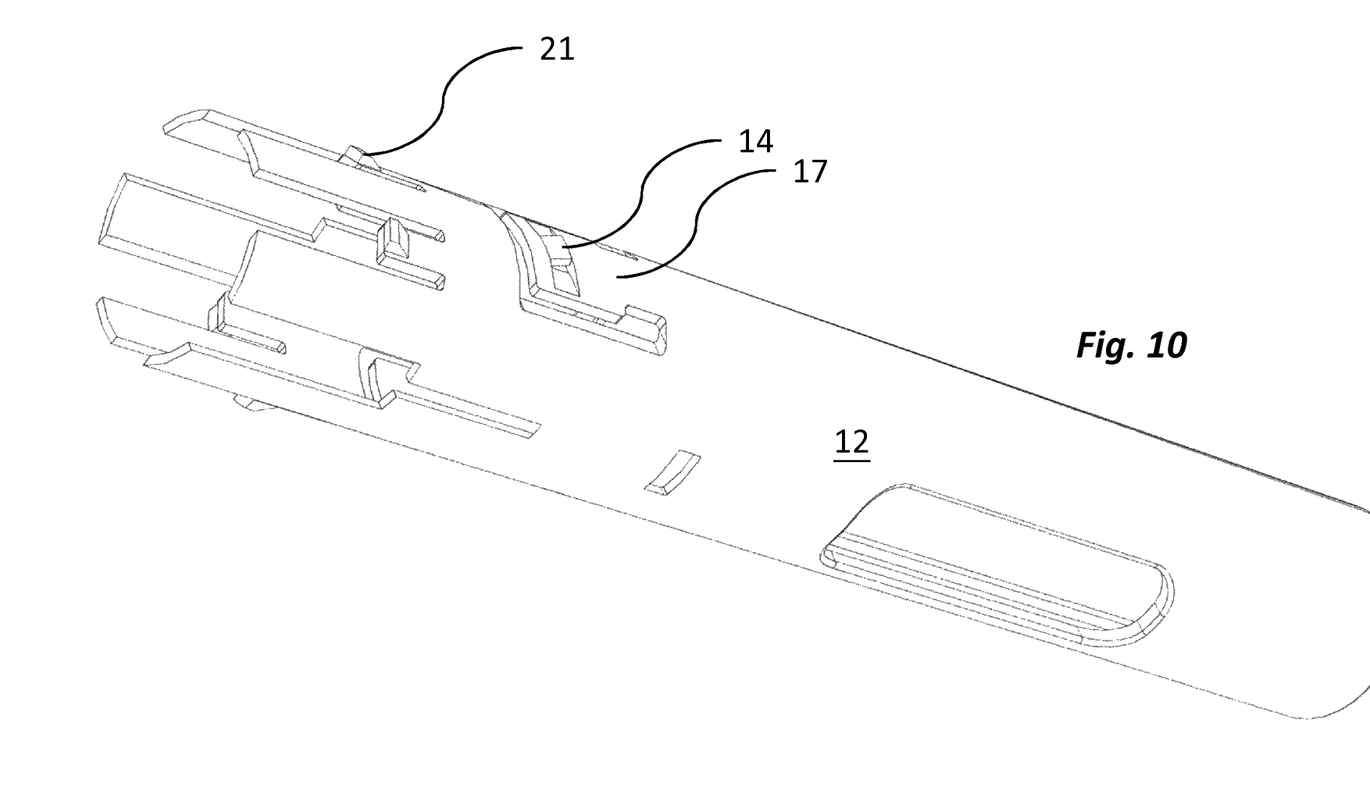
FIG. 10 shows a perspective view of the outer surface of the needle shield.

The needle shield mechanism comprises the needle shield 12, which has at least one, deflectable locking element 17, comprising outwardly directed protrusion 14, FIGS. 9, 10, that engages the ledge 15 of the housing 10, FIG. 9. The outwardly directed protrusion 14 has a chamfered surface which interacts with the ledge 15. The needle shielding mechanism further comprises the hold-and-release element 28 and the intermediate drive member 34, which prevent the deflectable locking elements 17 from flexing radially inward until the container carrier assembly has moved away from the initial position. Consequently, the deflectable locking elements 17 are held in place during most of the forward movement of the container carrier assembly, FIG. 5c. The movements of the container carrier assembly and of the needle shield 12 are effected by the second drive member 48 and by the first drive element 76, respectively.

Figure 6A:
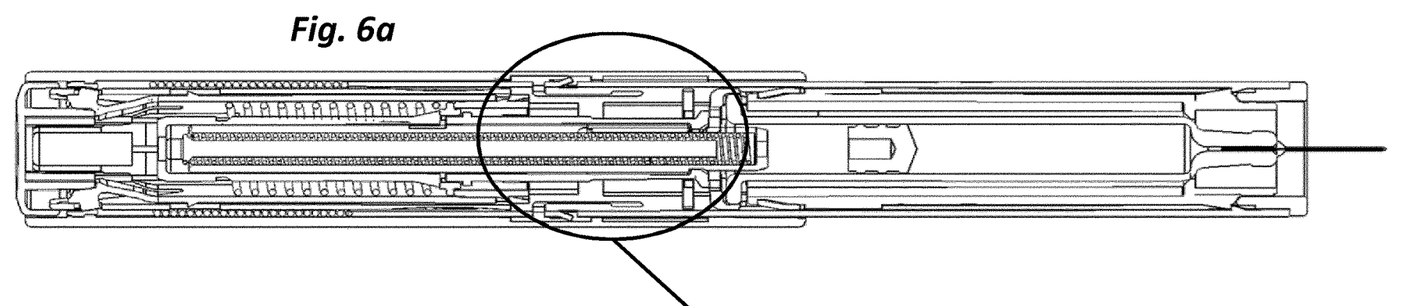
Figure 6B:
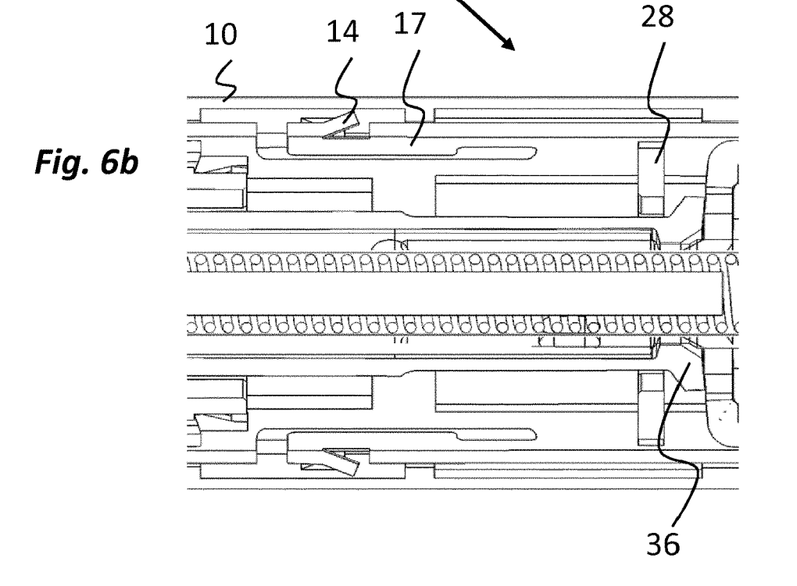

The hold-and-release element 28 and the intermediate drive member 34 move together with the container carrier 16 forward, from the initial position to the penetrating position during the penetration sequence. Towards the end of the penetration sequence, the container carrier assembly moves away from the deflectable locking element 17 comprising the outwardly directed protrusion 14. Without support of the intermediate drive member 34, the hold-and-release element 28 or the container carrier 16, the deflectable locking element 17 is allowed to move inwards under the bias of the first drive element 76, because the chamfered surface of the outwardly directed protrusion will slip off the ledge 15 as the deflectable locking element bends inwards under the bias of the second drive member 48. Consequently, the inwards movement disengages the protrusions 14 from the ledges 15 of the inner surface of the housing 10. However, as long as the medicament delivery device is pressed against the injection site, the needle shield 12 does not move. The unlocked needle shield 12 is shown in FIG. 6.

Figure 8A:
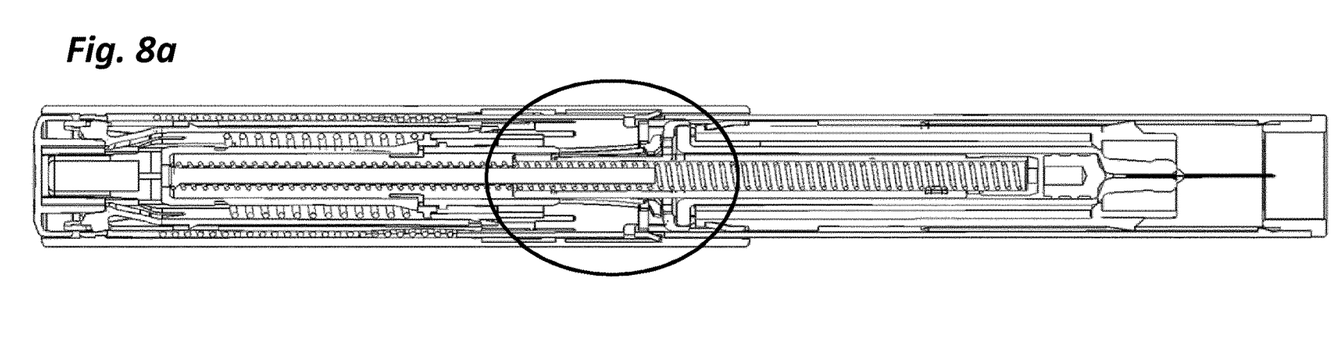
Figure 8B:
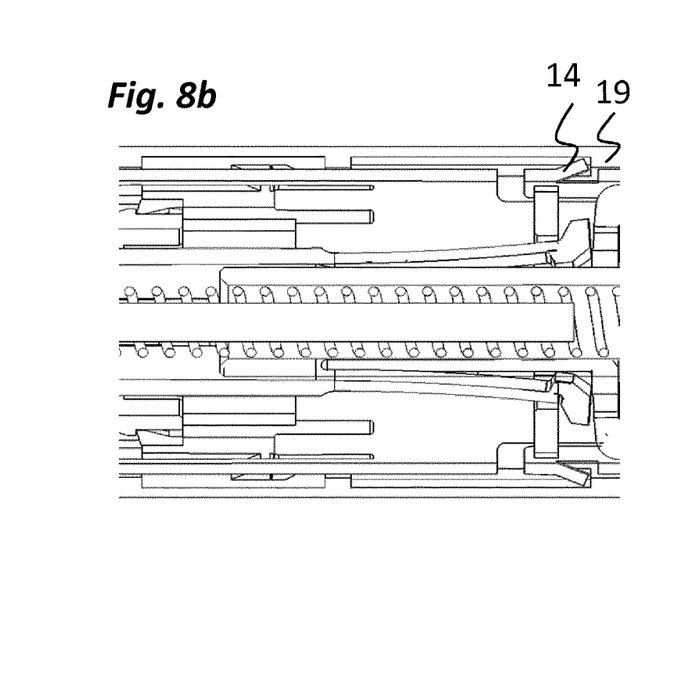
Figure 8C:
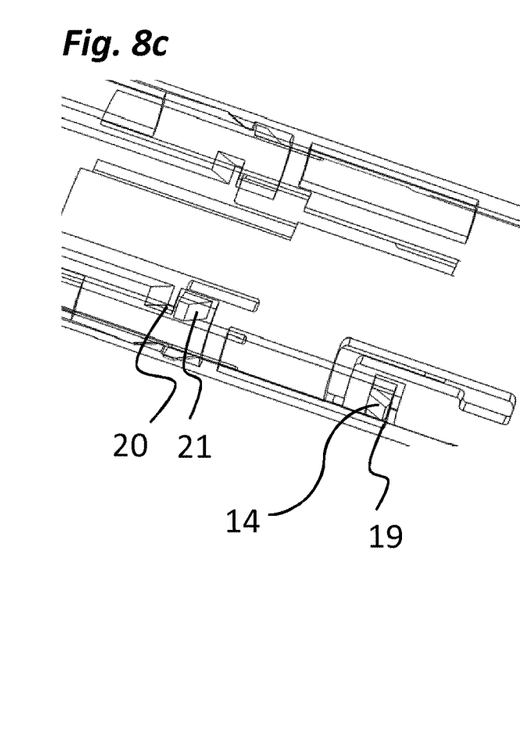

When the auto-injector is lifted from the injection site, the needle shield 12 moves forward relative to the housing 10 since the first drive element 76 is free to expand when the protrusion slips off the ledge 15. The needle shield 12 advances to the extended position, until the protrusion 14 of the needle shield 12 reaches a forward ledge 19 on the inner surface of the housing 10, FIG. 8b, 9. In the extended position, the deflectable locking element 17 of the needle shield 12 is once again adjacent the container carrier assembly, which rests in the penetrating position. The protrusion 14 is thereby prevented from disengaging the forward ledge to continue forward movement. In other words, the extended position is the most forward position of the needle shield 12 relative to the housing 10.

The needle 22 will be protected by the needle shield 12 in the extended position and a locking member 21 of the needle shield 12 will lock into a corresponding locking member 20 of the housing 10 to prevent movement of the needle shield 12 back towards the retracted state, see in FIGS. 8b, 8c, 9 and 10.

It can thus be seen that the needle shield 12 is released towards the end of the penetration sequence instead of at the end of the injection sequence. Therefore, the needle will be shielded once the injector is activated and then lifted, or removed from the injection site, regardless of whether the lifting action is accidental, e.g. before the full dose has been delivered, or intentional, at the end of the dose delivery sequence.

It is to be understood that the embodiment described above and shown in the drawings is to be regarded only as a non-limiting example of the invention and that it may be modified within the scope of the patent claims.

The invention claimed is:

1. A needle shield mechanism for an auto-injector, which needle shield mechanism comprises,
   a longitudinally elongated, generally tubular housing having a ledge on an inner surface, a forward end and a rear end,
   a generally tubular needle shield movably arranged in the housing between a retracted state and an extended position,
   a releasable spring-biased container carrier assembly for accommodating a medicament container,
   wherein the container carrier assembly is movably arranged in the housing and is movable relative to the housing from an initial position to a penetrating position, and is also movable relative to the needle shield,
   wherein the container carrier assembly prevents the needle shield from moving to the extended position when the container carrier assembly is in the initial position, and
   wherein the container carrier assembly allows the needle shield to move to the extended position when the container carrier assembly is in the penetrating position, and
   wherein the needle shield is spring-biased and comprises a deflectable locking element, which deflectable locking element comprises an outwardly directed protrusion that is radially deflectable and interacts with the ledge when the needle shield is in the retracted state, and
   wherein the container carrier assembly prevents the deflectable locking element from deflecting radially when the container carrier assembly is in the initial position and the needle shield is in the retracted state.

2. The needle shield mechanism for an auto-injector according to claim 1, wherein the container carrier assembly comprises a container carrier, configured to accommodate a medicament container.

3. The needle shield mechanism for an auto-injector according to claim 2, wherein the container carrier assembly further comprises an intermediate drive member fixedly connected to the container carrier.

4. The needle shield mechanism for an auto-injector according to claim 3, wherein either the container carrier or the intermediate drive member is adjacent and radially inside the deflectable locking element of the needle shield when the container carrier assembly is in the initial position and the needle shield is in the retracted state, thereby preventing the deflectable locking element from deflecting radially inwards.

5. The needle shield mechanism for an auto-injector according to claim 3, wherein either the container carrier or the intermediate drive member is in front of, and radially inside, the deflectable locking element of the needle shield when the container carrier assembly is in the penetrating position and the needle shield is in the retracted state, thereby allowing the deflectable locking element to deflect radially inwards, and allowing the needle shield to move to the extended position.

6. The needle shield mechanism or an auto-injector according to claim 5, wherein either the container carrier or the intermediate drive member is adjacently and radially inside the deflectable locking element of the needle shield when the container carrier assembly is in the penetrating position and the needle shield is in the extended position, thereby preventing the deflectable locking element from deflecting radially inwards.

7. The needle shield mechanism for an auto-injector according to claim 3, further comprising an injection mechanism comprising at least one flexible element arranged on the intermediate drive member.

8. The needle shield mechanism for an auto-injector according to claim 7, wherein the at least one flexible element is arranged with an inwardly directed ledge.

9. The needle shield mechanism for an auto-injector according to claim 8, further comprising a plunger having a recess, in which the inwardly directed ledge of the intermediate drive member is positioned when the container carrier assembly in the initial position.

10. The needle shield mechanism for an auto-injector according to claim 7, wherein the recess comprises a circumferential groove.

11. The needle shield mechanism for an auto-injector according to claim 1, wherein the outwardly directed protrusion comprises a chamfered surface which interacts with the ledge of the inner surface of the housing.

12. The needle shield mechanism for an auto-injector according to claim 1, wherein the needle shield comprises a locking member and the housing comprises a corresponding locking member.

13. The needle shield mechanism for an auto-injector according to claim 12, wherein the locking member and the corresponding locking member engage each other when the needle shield is in the extended position to lock the needle shield in the extended position.

14. The needle shield mechanism for an auto-injector according to claim 1, wherein the outwardly directed protrusion of the deflectable locking element interacts with a forward ledge of an inner surface of the housing when the needle shield is in the extended position.

15. The needle shield mechanism for an auto-injector according to claim 1, wherein the needle shield in the retracted state is movable between a partially extended position and a triggering position.

16. The needle shield mechanism for an auto-injector according to claim 15, wherein the container carrier assembly is configured to be released to move to the penetrating position when the needle shield is in the triggering position.

17. A needle shield mechanism for an auto-injector, which needle shield mechanism comprises,
   a longitudinally elongated, generally tubular housing having a forward end and a rear end,
   a generally tubular needle shield movably arranged in the housing between a retracted state and an extended position,
   a releasable spring-biased container carrier assembly for accommodating a medicament container,
   wherein the container carrier assembly is movably arranged in the housing and is movable relative to the housing from an initial position to a penetrating position, and is also movable relative to the needle shield,
   wherein the container carrier assembly prevents the needle shield from moving to the extended position when the container carrier assembly is in the initial position, and
   wherein the container carrier assembly allows the needle shield to move to the extended position when the container carrier assembly is in the penetrating position, and wherein the needle shield is spring-biased and comprises a deflectable locking element, which deflectable locking element is radially deflectable, and wherein a component of the container carrier assembly, either a container carrier or an intermediate drive member, is adjacent and radially inside the deflectable locking element of the needle shield when the container carrier assembly is in the initial position and the needle shield is in the retracted state, thereby preventing the deflectable locking element from deflecting radially inwards.

* * * * *